US006201978B1

(12) United States Patent
Buschmann

(10) Patent No.: US 6,201,978 B1
(45) Date of Patent: Mar. 13, 2001

(54) APPLICATOR FOR PULSOXYMETRIC SENSOR WITH TORQUE LIMITER

(76) Inventor: Johannes Buschmann, Hohenaschauer Strasse 92, D-81669 München (DE)

( * ) Notice: Subject to any disclaimer, the term of this patent is extended or adjusted under 35 U.S.C. 154(b) by 0 days.

(21) Appl. No.: 09/269,441

(22) PCT Filed: Sep. 23, 1997

(86) PCT No.: PCT/EP97/05213

§ 371 Date: Mar. 26, 1999

§ 102(e) Date: Mar. 26, 1999

(87) PCT Pub. No.: WO98/13678

PCT Pub. Date: Apr. 2, 1998

(30) Foreign Application Priority Data

Sep. 26, 1996 (DE) ........................................ 196 39 648

(51) Int. Cl.[7] .................................................. A61B 5/00

(52) U.S. Cl. ........................................ 600/338; 600/376

(58) Field of Search .................................. 600/313, 310, 600/322, 323, 325, 327, 338, 339, 340, 341, 372, 376, 373, 511

(56) References Cited

U.S. PATENT DOCUMENTS

| | | | | |
|---|---|---|---|---|
| 5,361,757 | * | 11/1994 | Smith et al. | 600/338 |
| 5,388,579 | * | 2/1995 | Dowd et al. | 600/376 |
| 5,423,314 | * | 6/1995 | Schmid | 600/376 |

* cited by examiner

*Primary Examiner*—Eric F. Winakur
(74) *Attorney, Agent, or Firm*—Pendorf & Cutliff

(57) ABSTRACT

The invention relates to an applicator for sensors to be used in medicine, which serves to screw in a sensor in the skin of a living organism, specially in a non-observable area, e.g. the head skin of a child in the womb. In this respect the torque while screwing the sensors into the tissue of the patient is limited to least to a maximum, while ensuring at the same time that the torque is kept to an indispensable minimum. The applicant (1) interacts with a torque limiter (5) and comprises a device that makes it possible to detect the threshold value of the torque limiter.

25 Claims, 3 Drawing Sheets

17
4
18
7
13
12
10
11
19
16
9
8
20
14

7
13
13
10
10
18
4
17
8

APPLICATOR FOR PULSOXYMETRIC SENSOR WITH TORQUE LIMITER

BACKGROUND OF THE INVENTION

1. Field of the Invention

The invention relates to an applicator for sensors used in the field of medicine.

2. Description of the Related Art

In the field of medicine it is known to insert sensors, especially spiral sensors, into the skin of the patient by rotation, i.e., to screw a spiral sensor with its usually very sharp front end into the skin of the patient in a spiral type motion consisting of application-pressure and torque.

This is the case for example with the wide-spread fetal scalp electrodes which are used to anchor a sensor in the scalp of an unborn child in order to measure the ECG of the unborn child after membranes are ruptured.

Optical sensors can be housed in the tip of such spiral sensors, too, for example for fetal pulse oximetry, with the help of which a direct monitoring of the oxygen saturation in the blood of the unborn child can be established.

Such a sensor is disclosed in the DE-C 3810 008. C1

Since the spiral sensors are applied at a location which is out of view, that is to say behind the vagina of the mother within the uterus, it is a problem for the user to apply these spiral sensors with the correct amount of torque. If too much of a torque is applied, injuries of the fetal scalp are possible as well as a damage of the sensor and the applicator respectively or the perfusion at the site of the application can be restricted by too high an axial pressure of the sensor relative to the patient.

If too small of a torque is applied, the sensor is only poorly anchored in the skin of the patient and it comes loose due to the dynamic stresses occurring during the delivery and the vaginal examinations during the delivery respectively. Moreover too weak an application results in distortions of the signals derived from the sensor.

The application of the correct torque gets even more difficult because the sensor is located at the front end of a thin, long plastic rod or plastic tube respectively and because the user is able to turn only the rear end of this rod-like applicator. With a 20 cm long but just 2 or 3 mm thick rod the bending and the torsion of this rod-like applicator limits the user's feeling for the correct torque.

It is therefor the object of the present invention to provide an applicator which limits the torque during the insertion of the sensor into the tissue of the patient at least in respect to a maximal torque on the one hand, but on the other hand guarantees a necessary minimal torque during the application as well.

Thus the minimal torque guaranteed by the torque limiter may coincide with maximal torque to form a threshold value, that is to say, the very threshold value at which the torque limiter slips.

SUMMARY OF THE INVENTION

By providing the torque limiter in or on the applicator it is guaranteed that during the insertion no torque higher than the one the torque limiter is adjusted to can be applied.

In addition it is important that there is a perceptibility of the slipping through phenomenon of the torque limiter, that is to say, a device that allows to see the slip through phenomenon or at least to sense it with the operating hand.

A torque limiter of this type can be set to both a maximum and a minimum torque so that the torque limitation towards the minimal value avoids too soft an application and thus likewise too poor a fixation of the sensor in the tissue of the patient.

An especially simple embodiment of a torque limiter is represented by a sliding clutch which can be either mechanical, i.e. a force fitting or form-fitting operating by friction, as well as a magnetic, especially an electromagnetic, sliding clutch. The upper and lower limits of the torque can be easily adjusted, easily controlled and can be quickly deactivated in an easy manner too, by electrically influencing the magnetic forces of the sliding clutch.

At a first glance it would seem to be useful to position the torque limiter, for example the sliding clutch, as close as possible to the sensor, that is to say, at the front or the sensor end of the applicator, between the applicator and the sensor, in order to exclude the influence of the twistable applicator on the torque applied to the patient.

The drawback of this solution lies in the fact that the torque limiter is, during the fetal application, within the maternal body and thus under the influence of body fluids and mechanical pressure of the surrounding vagina, which could undesirably influence the function of the torque limiter.

If the torque limiter is positioned at the rear handling end of the applicator rod which is positioned outside of the body of the mother during the application, those interfering influences by body fluids and so on are avoided. In order to avoid a disturbance on the torque at the sensor caused by the twistable applicator rod which is positioned between torque limiter and sensor, the maximal torque applicable by the torque limiter must be lower than the torque by which the applicator rod collapses. A slight torsion of the applicator rod is harmless, since this torsion just causes an angle deviation between the handling end and the sensor end of the applicator rod but does not change the level of the torque having an influence on the patient, as long as this torque is the maximal applicable torque to which the torque limiter is preadjusted.

Such a fixed, preadjusted torque based on the torque limitation has a variety of advantages:

The evaluating devices linked to the sensor provide meaningful values since both the electric and the optic coupling to the tissue is more reliable, the influence on tissue perfusion of the patient remains minimal, its tissue physiology remains undisturbed and the traumatization of the tissue remains minimal. In addition the probability of tissue injuries of the patient becomes minimal so that all this can be used as a legal argument during a dispute with the patient since this torque limiter excludes the application of too high a torque and at the same time too low a torque. Further, the destruction of the sensor due to overstraining is avoided as well as a need for a reapplication after a too superficial fixation due to too small an application-torque. Also, less experienced users can feel safe beginning with the first experience with application.

When positioning the torque limiter in the handle of the applicator, especially a mating with a handle end is recommended since it can be disconnected from the single-use-applicator and is reusable.

Also the torque limiter can be positioned at the transition between the applicator rod and the grip part or between two parts of the handling part which are moveable relative to each other that is to say the applicator flange to which the handling end of the applicator rod can be attached and the handle which the user holds in his hand.

Further it is important, that the handle has a diameter which resembles the common applicators without a torque limiter attached thereto, in order not to change the accustomed subjective feeling for the torque to which the torque limiter is preset by a different handle diameter. This may cause the users to lose confidence in the torque limiter.

If the torque limiter is positioned at the front end of the applicator i.e. for example between the applicator rod and the sensor, then due to the single use concept of the applicator just a mechanically simple, easily and inexpensively producible form can be considered. This could be for example a concept where the front end of the applicator and the part which directly carries the sensor interact as a mechanical sliding clutch so that one of the parts has a non-round exterior shape, e.g. an ellipse or a polygonal shape, and is surrounded by another part which has an analog interior shape.

If one of the components, especially the surrounding component, shows a relatively high material-elasticity, and if there is enough play between the inner and outer outlines, the inner part will slip through relative to the exterior part at a maximum applicable torque, which creates the maximum torque limitation. After the application of this maximal torque the applicator rod is removed as usual, so that just the sensor and the cable leading to and from the sensor remain on the patient.

To position a magnetic sliding clutch within the one way item, that is to say between applicator and sensor would be too costly.

Such a solution however is feasible in the form of a reusable item, which is made of a stable metal in contrast to the applicator which usually consist of plastic. At the applicator flange of the handling part, the rear handling end of the applicator rod can be quickly and easily attached by engagement, attachment with a setscrew, etc. The handling part consists of two components, movable relative to each other, which house a sliding clutch between themselves.

This sliding clutch can be of the formerly described type or of a more sophisticated mechanical sliding clutch comprising springloaded engaging parts, or a magnetic or electromagnetic sliding clutch respectively.

In a magnetic sliding clutch the engaging magnets can be positioned at the opposing areas of the applicator flange that is to say, of the handle. If all magnets of one part are positioned so that they oppose with their e.g. positive ends versus the other part and the magnets of the other part are mounted in reverse, then the applicator flange and the handling part will have a minimum distance relative to each other due to the attracting power of the magnets, that is to say the user, who additionally needs to push in an axial direction (during the application), applies this axial pressure directly onto the patient's tissue, without thereby initially reducing a functional distance between the parts of the sliding clutch.

When positioning the magnets with opposing directed faces, a well defined distance between these facing areas must be set, making use of a spacer-disc, which is e.g. made of plastic, in order to adjust the attraction power for mass production of the handling part, since the attraction power greatly varies with distance changes of the magnets, which determine the maximal achievable torque.

This problem does not exist if the magnets are housed in areas radially opposite to each other, one area belonging to the applicator flange, the other area belonging to the handle, and these components are positioned next to each other in order to maintain the same radial distance relative to each other.

Such a magnetic sliding clutch provides a torque limitation avoiding maximal torque forces. If electromagnets are used as the magnets, the maximum transmittable torque can be adjusted. If with such a magnetic solution an additional minimal torque is to be provided, this can be achieved for example with a friction between the two components of the sliding clutch which needs to be overcome, as long as there is no magnetic flow during the rotation of the components of the sliding clutch relative to each other. This for example is possible if just one or only very few pairs of magnets are positioned along the circumference of the sliding clutch, so that there is no magnetic interaction in the area in between, but just the mechanic friction between the two components of the sliding clutch. Due to the axial pretension between the two components this sliding clutch can provide a torque limitation towards the minimal values.

BRIEF DESCRIPTION OF THE DRAWINGS

An embodiment according to the invention is described hereinafter in greater detail with reference to the drawings. In the following

DETAILED DESCRIPTION OF THE INVENTION

Figure 1A:
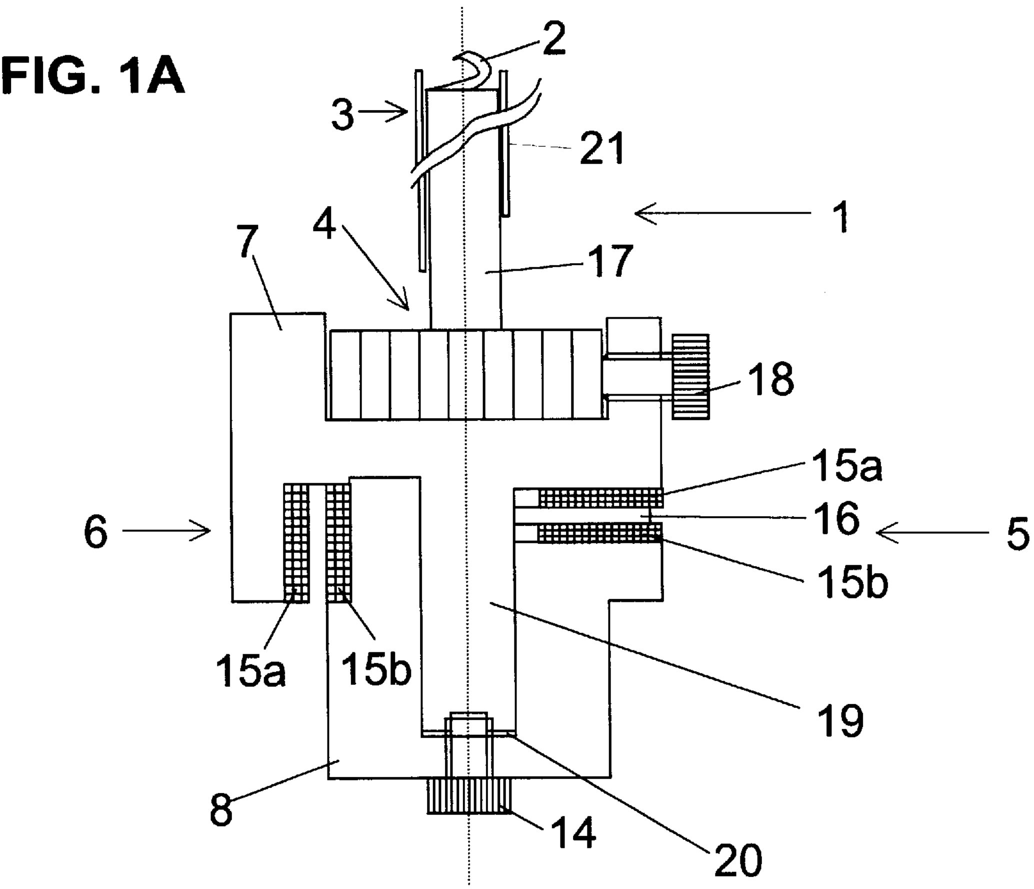
FIG. 1A: shows a side view of an applicator with a magnetic sliding clutch

FIG. 1A shows an applicator 1, which includes a very long and slender applicator rod 17 slidable within protective tube 21 which at the back or hand manipulation end 4 exhibits a widening or thickening, with which the applicator rod 17 is fixable by means of clamping screw 18 as well as rotatably fixed in a corresponding face recess of a manipulation part 6, which contains the torque limiter 5.

At the front free end, the sensor end 3, there is seated in the applicator rod 17 the sensor 2, which has the shape of a rotating spiral with a very pointed, sharpened end. With this tip the spiral shaped sensor 2 can be screwed into for example the scalp of an unborn child.

The hand manipulation part 6 is comprised besides the applicator flange 7, in which the hand manipulation end 4 of the applicator rod 17 is received, of a hand grip part 8, which the user holds in his hand. The applicator flange 7 exhibits towards the back, on the side facing away from the applicator rod 17 an outward projecting extension 19 with round cross-section, upon which the hand grip part 8 by means of a corresponding central blind hole is seated and rotatably mounted.

With the help of a pretensioning adjuster 14 in the form of a central screw the axial pretensioning between the applicator flange 7 and the hand grip part 8 can supplementally be influenced from the back side of the hand grip part 8 through this into the projection 19 of the applicator flange 7.

Figure 1B:
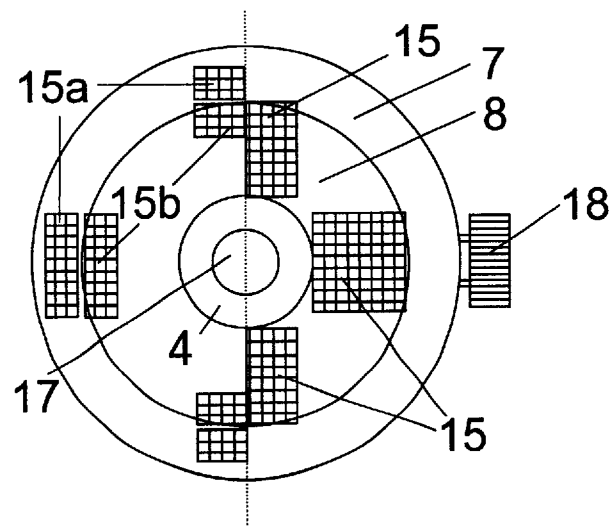
FIG. 1B: shows a tip view of an applicator with a magnetic sliding clutch

In the right half of FIG. 1, there are positioned—radial outside the projection 19—the applicator flange 7 and the hand grip part 8 with surfaces facing against each other, wherein magnets 15*a*, 15*b* are oriented against each other upon these opposing lying faces. As FIG. 1*b* shows, there are herein on each of the faces in 90° separation four such magnets 15*a* or as the case may be 15*b* provided, this so that the two oppositely directed magnets respectively attract each other.

Between the applicator flange 7 and the hand grip part 8, which in this mode and manner are axially drawn towards each other to contact, a spacer ring 16 is interposed. The thickness of this spacer ring 16 determines in the attracting magnet pairs 15*a*, 15*b* their respective magnetic attraction force, which at a different separation between the magnets 15*a* and 15*b* likewise strongly would vary.

If one would securely hold the applicator flange 7, and rotate the hand grip part 8, so a predetermined force is necessary in order to rotate a particular magnet 15*a* past a initially oppositely lying magnet 15*b* and to overcome the therebetween existing magnetic attraction force, whereupon the rotated magnet 15*b* will position itself opposite to the next magnet 15*a* in the rotation direction.

When for screwing in of the sensor 2 in the tissue of the patient the user no longer takes the applicator rod 17, but rather exclusively the hand grip part 8 of the hand manipulator part 6 and turns, it is insured, that the sensor 2 never is screwed in with greater torque than is necessary for slipping past the rotation moment limiter 5, that is, for relative turning of the magnet 15*b* with respect to the magnets 15*a*.

If one supplementally employs the applicator 1 so that the user is instructed to rotate the hand grip part 8 at least so far, until at least one relative rotation between the magnets 15*a* and 15*b* has occurred, so it is further insured, that the sensor 2 is screwed in with a torque, which corresponds at least to that torque necessary for the overcoming of the magnetic forces.

In this case the minimal exercised torque corresponds at the same time to the maximal exercised torque.

In the left half of FIG. 1, in contrast to the right figure half, the magnets 15*a* and 15*b* are positioned radially opposing. For this purpose one magnet 15*a* is provided along the outer circumference of the hand grip part 8 and the outer circumference of which lies opposite to an inner circumference of an at the back end face side cartridge like bored out applicator flange 7, in which the opposing magnets 15*a* are provided with the same positioning over the circumference.

Since the grip part 8 is mounted rotatably with small as possible slack or play on the projection 19 of the applicator flange 7, the magnets 15*a* and 15*b* always assume the same radial separation from each other, so that the employment of a spacer disk 16, which with respect to its thickness is essential in the right half of FIG. 1*a*, is not required, and therewith also the wearing out thereof results in no changes in the effective torque. However in the case of the embodiment shown in the left half of the figure, the production expenditure for the hand manipulation part 6 is greater.

Figure 2A:
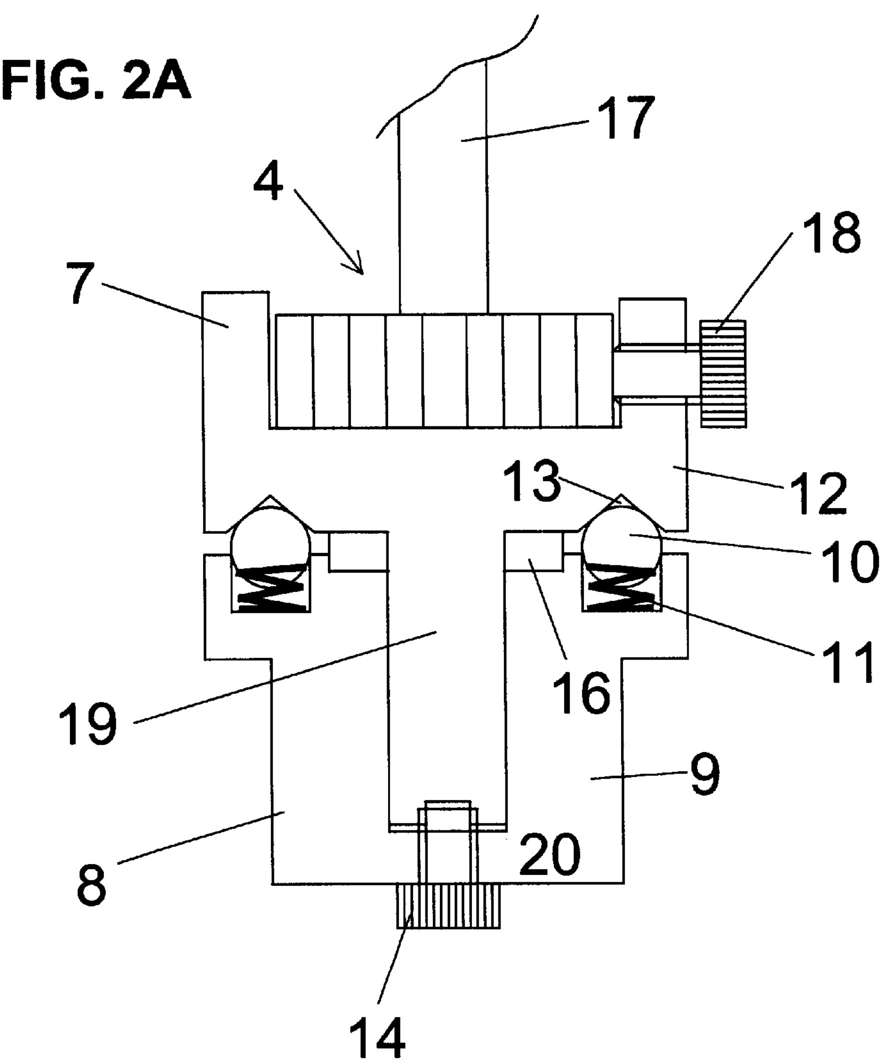
FIG. 2A: shows a side view of an applicator with a mechanic sliding clutch

FIG. 2A shows in comparison a mechanical variant of the slip clutch, which serves as torque limiter 5.

In contrast, the hand manipulation part 6 is comprised of a flange applicator 7 and a hand grip part 8 mounted rotatably with respect thereto upon the end projection 19.

Herein the design of the applicator flange 7 as well as the securing of the applicator rod 17 as well also the mounting of the hand grip part 18 with respect to the applicator flange corresponds overall with the solution according to FIG. 1.

The hand grip part 8 serves herein as base part 9 of a slip clutch, while the applicator flange 7 functions as counterpart 12 of the slip clutch. In the base part 9 detent or engagement bodies 10, for example balls, are pre-tensioned in corresponding recesses by means of respectively a spring 11 in the direction away from the base part, so that the detent or engagement bodies 10 project out from the base part 9, in the axial direction shown in FIG. 2. In the oppositely lying face of the counterpart 12 there are formed recesses 13, in which the engagement bodies 10 partially penetrate into and there form fittingly lock. The direct axial separation between the base part 9 and the counter part 12 is again maintained by an axial working pre-tensioning disk 14, as in FIG. 1 an axially screwed in screw, since without this the spring 11 of the locking body 10 would push the base part 9 and the counterpart 12 apart from each other.

Radially outside of the locking part 10 a spacer ring 16 is introduced between the base part 9 and the counterpart 12 and with the help of a pre-tensioning disk 14 is somewhat clamped.

In order to rotate the base part and the counterpart 12, that is, the hand grip part 8 and the flange applicator 7, relative to each other, the forces of the springs 11 must be overcome, which produces the maximal rotational torque limitation.

Figure 2B:
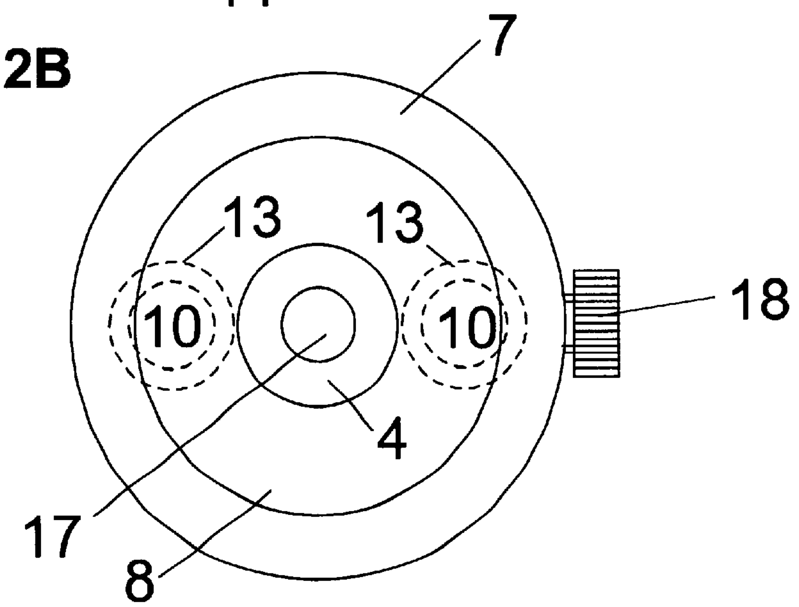
FIG. 2B: shows a top view of an applicator with a mechanic sliding clutch

When, as shown in FIG. 2*b*, over the circumference only two such engagements are provided, then the torque to be brought to bear in the rotation area between the two engagement parts corresponds only to the friction between the hand grip part 8 and the flange applicator 7, that is, the sliding rubbing between the spacer ring 16 and the friction with respect to the engagement part 10. This engagement resistance represents the minimal rotational torque limitation by screwing of the pre-tensioning adjuster 14 the distance ring 16 is wedged more strongly between the two adjacent parts and therewith the friction is increased, whereby also the minimal necessary torque for screwing in of the sensor 2 is increased.

The force for overcoming the locking and therewith the maximal possible torque to be brought to bear is not necessarily increased thereby, when the spring characteristic of the spring 11 is so selected, that small axial changes of base part 9 and counterpart 12 do not bring about an increase in the axial pressure force upon the engagement part 10 as consequence. Of course, the form fittingness of the engagement part 10 and the engagement recesses 13 must be so selected, that for overcoming this engagement or locking necessary forces basically lie higher than the pure rubbing frictional forces on the basis of the friction between the spacer ring 16 and the engagement part 10.

Figure 3:
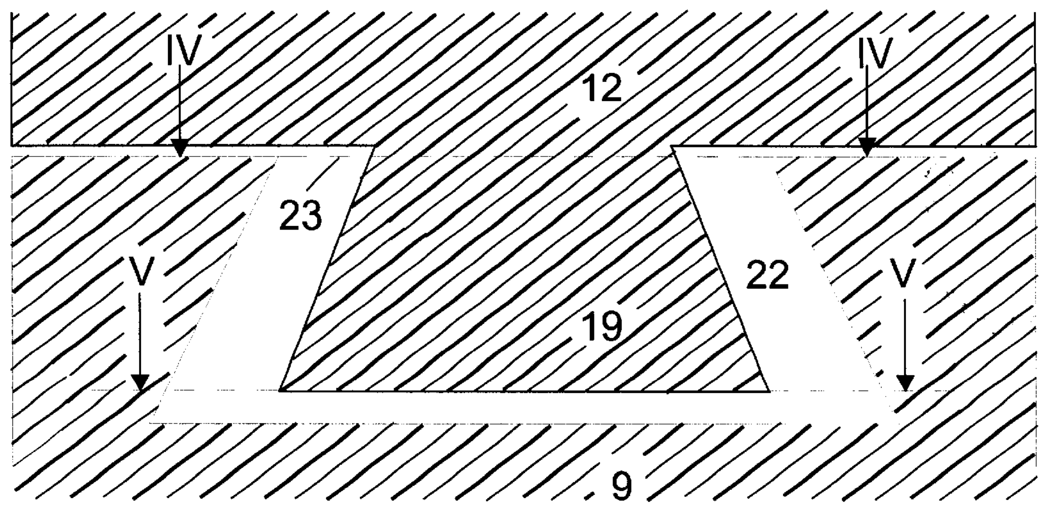
FIG. 3: shows a side view of longitudinal section through a mechanical sliding clutch.
Figure 4:
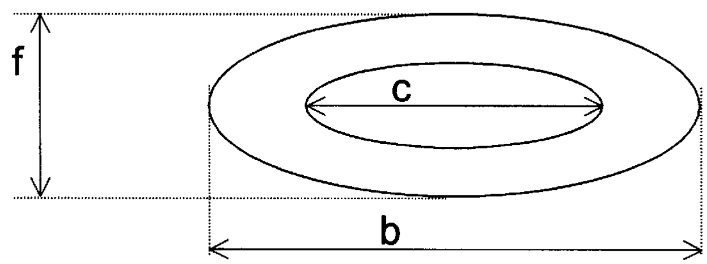
FIG. 4 shows a longitudinal cross section through a sliding clutch along the lines IV—IV according to FIG. 3
Figure 5:
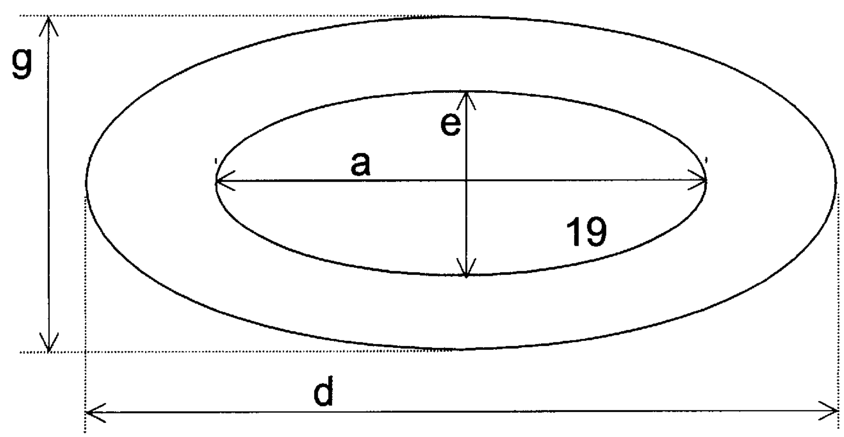
FIG. 5: shows a longitudinal cross section through a sliding clutch along the lines IV–VI according to FIG. 3.

FIGS. 3–5 show a further variant of a mechanical slip clutch, which without moving parts essentially is based upon material elasticity.

FIG. 3 shows a longitudinal section through such a slip clutch, which is comprised of a base part 9 and a counterpart 12. Therein there can again—as already discussed on the basis of FIG. 2*a*—base part 9 and counterpart 12 of the applicator flange 7 or as the case may be the hand grip part 8, or also reversed, form the hand manipulation part 6 which carries the applicator 1.

FIG. 3 shows, that one of the parts, for example the counterpart 12, exhibits an in axial direction running projection 19, which exhibits a changing cross-section, namely from its base at the counterpart 12 is relatively small and continuously increases in cross-section towards the free end.

The cross-section of the projection 19 is elliptic, and this with a larger diameter "a" and small diameter "e" at the position of the larger cross-section, that is at the free end of the projection 19, which is shown in the sectional representation V—V in FIG. 3 and in FIG. 5. At the juncture of the projection 19 on the counterpart 12 the larger diameter with "c" is significantly smaller than at the free end indicated with "a" which is shown in the sectional representation IV—IV in FIG. 3 and in FIG. 4.

The counterpart 12 is seated with this projection 19 in a recess 22 in the base part 9, which exhibits an analogous, however in cross-section larger inner contour and a depth, which is somewhat larger than the axial length of the projection 19.

Since additionally the largest cross-section of the projection 19 on its free end is slightly smaller than the smallest cross-section of the recess 22, which is situated at the opening 23 side facing the counterpart 12, the projection 19 can, in the correct rotation position or orientation, be completely introduced into the recess 22, so that the base part 9 and the counterpart 12 at their faces lie planar against each other. The cross-section of the recess 22 is therein so selected, that in this into each other assembled condition the smallest diameter "g" of the elliptic recess 22 is smaller than the largest diameter "a" of the elliptic post 19 at the same axial position.

When the cross-section of the projection 19 changes in the axial course just as fast as the cross-section of the recess 22, that is their flanks have the same pitch with respect to the axial longitudinal direction, then this condition is valid for the entire length of the projection 19, and not only at the free end as shown in FIG. 5.

A relative turning about the longitudinal direction between base part 9 and counterpart 12 about 90° or more is thereby only possible, when by material elasticity of either the larger diameter of the projection 19 and/or the smaller diameter of the surrounding inner contour of the recess 22 can be so deformed, that a slipping through of the two parts with respect to each other is possible.

Therewith besides the material elasticity of the projection 19 of the counterpart 12 or, as the case may be, the base part 9, also the size differential between the larger diameter of the projection 19 and the at the same position existing smaller diameter of the elliptic cross-section of the recess 22 determine or dictate the force, which is necessary for turning through of this form locking or form engaging mechanical slip clutch.

What is claimed is:

1. Torque limiting applicator for screwing a sensor into the skin of a living being, comprising:

an applicator (1) having a proximal end and a distal end, and adapted for receiving a sensor at said distal end; and a torque limiter (5) adapted for engagement with said proximal end of said applicator (1) and:

(a) adapted for transmission at least a minimal torque;

(b) adapted for slipping-through upon exceeding a maximal torque value, wherein said minimal torque is the torque required by an operator to insert and securely anchor said sensor into the skin, and wherein said maximal torque value is a torque value below the value at which injury of the skin is caused by overtorquing said sensor into said skin; and (c) providing a slipping-through feedback upon exceeding the maximal torque value of the torque limiter (5).

2. Applicator according to claim 1, wherein said torque limiter (5) is adapted to provide the operator with a tactile perception of the slipping-through phenomenon at the maximal value of the torque limiter (5).

3. Applicator according to claim 1, wherein the applicator (1) is basically rod-shaped, and further adapted for releasable seating of a sensor at said distal end, and having a proximal end (4) adapted for manipulation by hand.

4. Applicator according to claim 3, further comprising a manipulation part (6) removably positioned at the proximal end (4) of the applicator rod (17) and wherein the manipulation part (6) is reusable.

5. Applicator according to claim 1, wherein the applicator (1) is designed as a single use item.

6. Applicator according to claim 1, wherein the torque limiter (5) is positioned between the applicator rod (17) and the sensor (2).

7. Applicator according to claim 6, wherein the manipulation part (6) includes an applicator flange (7) and a hand grip part (8), and wherein the torque limiter (5) is positioned between the applicator flange (7) and the hand grip part (8).

8. Applicator according to claim 7, wherein the slip clutch comprises means for limiting torque transfer between the applicator flange (7) and the hand grip part (8) of the manipulation part (6) of the base part (9).

9. Applicator according to claim 7, wherein the applicator flange is configured to retain a manipulable enlarged end of a disposable non-torque limiting sensor applicator, and the hand grip part (8) has an outer circumference with approximately the same diameter as the outer diameter of the manipulable enlarged end.

10. Applicator according to claim 1, wherein the torque limiter (5) is positioned at the proximal end (4).

11. Applicator according to claim 10, further comprising a manipulation part (6), and wherein the torque limiter (5) is positioned between the proximal end (4) of the applicator rod (17) and the manipulation part (6).

12. Applicator according to claim 11, wherein the applicator flange (7) is rotatably connected with the hand grip part (8) but fixed in the axial direction with respect to the hand grip part (8).

13. Applicator according to claim 12, wherein the torque limiter comprises a magnetic slip clutch having opposing sets of permanent magnets.

14. Applicator according to claim 12, wherein the torque limiter comprises a slip clutch having a mechanical coupling with a base part (9) and a counterpart (12) rotatable mounted thereto, and further comprising a projection (19) having an outer contour, said projection (19) on one of said basepart (9) and counterpart (12), and a recess (22) having an inner contour, said recess (22) in the other of said base part (9) and counterpart (12), wherein the projection (19) has a non-round outer contour and the recess (22) has an analog shaped multi-sided inner contour, said projection (19) being at least partially enclosed and rotatably mounted in said recess, and wherein at least one of the base part (9) and the counterpart (12) is formed of a material possessing a sufficient material elasticity whereby torque-produced deformation of a non-round contour produces a relative rotation between the base part and counterpart.

15. Applicator according to claim 14, further comprising a pre-tensioning disk (14), wherein the pre-tensioning in the axial direction between the base part (9) and the counterpart (12) is adjustable by means of the pre-tensioning disk (14).

16. Applicator according to claim 12, wherein the torque limiter comprises a magnetic slip clutch comprising a base part (9) and an opposing counterpart (12) rotatably secured thereto, wherein at least first and second magnets **(15*a*, 15*b*) are provided directed against each other in the two opposing faces of the base part (9) and the counterpart (12)**.

17. Applicator according to claim 16, further comprising a distance ring (16) of non-magnetic material positioned in the axial direction between the base part (9) and the counterpart (12), the distance ring (16) producing a friction force between the base part (9) and counterpart (12) comprising a minor portion of the maximal torque value.

18. Applicator according to claim 16, wherein the magnets **(15*a*) are all with the same polarity oriented against the counterpart (12) and the magnets (15*b*) are oriented all with the opposite pole directed against the magnets (15*a*) of base part (9)**.

19. Applicator according to claim 16, wherein the base part (9) and the counterpart (12) have concentric facing ring surfaces, and wherein said first magnet **(15*a*) is radially concentric to second magnet (15*b*), wherein said first and second magnets (15*a*,b) are positioned on ring surfaces of the base part (9) and the counterpart (12)**, respectively.

20. Applicator according to claim 19, wherein the counterpart (12) exhibits a projection (19) with elliptical cross-section and a free end, of which the cross-section dimensions increases towards the free end, and the base part (9) exhibits an analogous shaped larger recess (22) with analogous inner contour, wherein the largest cross-section of the projection (19) of the counterpart (12) is slightly smaller than the smallest cross-section of the recess (22) of the base part (9);

wherein rotation of projection (19) of the counterpart (12) within the recess (22) results in at least one rotative position where the maximum diameter of the projection (19) is larger than the smallest diameter of the recess (22) at corresponding locations.

21. Applicator according to claim 20, wherein the cross-section of the projection (19) and the cross-section of the recess (22) continuously increase in the axial direction from the base of the projection (19) at the counterpart (12) towards the free end thereof.

22. Applicator according to claim 11, wherein the torque limiter (5) is one of a mechanical slip clutch, force slip clutch and form locking slip clutch.

23. Applicator according to claim 11, wherein the torque limiter comprises a mechanical slip clutch including a base part (9) and an opposing rotatably mounted counterpart (12), wherein an engagement part (10) projects from one of the base part (9) and counterpart (12), and detent recesses (13) are formed in the other of the base part (9) and counterparat (12), the engagement part (10) which in the direction of its projection is pre-tensioned, and configured to engage in detent recesses (13) formed in the opposing part.

24. Applicator according to claim 1, wherein the torque limiter (5) includes a device for providing tactile feed back of slipping through.

25. Applicator according to claim 1, wherein the projection (19) is shorter in the axial direction than the depth of the recess (22).

* * * * *